(12) United States Patent
Gittard et al.

(10) Patent No.: US 11,213,392 B2
(45) Date of Patent: Jan. 4, 2022

(54) BELT FOR APPLYING PRESSURE TO A BODILY ORGAN

(71) Applicant: Muffin Incorporated, West Lafayette, IN (US)

(72) Inventors: Shaun Davis Gittard, Winston-Salem, NC (US); John C. Sigmon, Jr., Winston-Salem, NC (US); Gregory James Hardy, Asheville, NC (US); Jeremy T. Newkirk, West Lafayette, IN (US); Neal E. Fearnot, West Lafayette, IN (US); William J. Havel, West Lafayette, IN (US); Rita Hadley, Otterbein, IN (US); Yun Zhou, Eden Prairie, MN (US)

(73) Assignee: Muffin Incorporated, West Lafayette, IN (US)

( * ) Notice: Subject to any disclaimer, the term of this patent is extended or adjusted under 35 U.S.C. 154(b) by 420 days.

(21) Appl. No.: 16/174,779

(22) Filed: Oct. 30, 2018

(65) Prior Publication Data

US 2019/0151092 A1 May 23, 2019

Related U.S. Application Data

(60) Provisional application No. 62/580,033, filed on Nov. 1, 2017.

(51) Int. Cl.
*A61F 2/24* (2006.01)
*A61B 5/00* (2006.01)
*A61B 17/04* (2006.01)

(52) U.S. Cl.
CPC .......... *A61F 2/2481* (2013.01); *A61B 5/6831* (2013.01); *A61B 17/0487* (2013.01);
(Continued)

(58) Field of Classification Search
CPC ............ A61F 2/2481; A61F 2220/0075; A61F 2250/001; A61F 2230/0065;
(Continued)

(56) References Cited

U.S. PATENT DOCUMENTS

2002/0156526 A1* 10/2002 Hlavka ................ A61F 2/2445
623/2.11
2003/0167071 A1* 9/2003 Martin ............... A61B 17/0469
606/232
(Continued)

FOREIGN PATENT DOCUMENTS

WO WO 2000/69323 11/2000
WO WO 2001/91667 A2 12/2001
(Continued)

OTHER PUBLICATIONS

International Application No. PCT/US2018/058454 International Search Report and Written Opinion, dated Feb. 12, 2019.

*Primary Examiner* — Kaylee R Wilson
(74) *Attorney, Agent, or Firm* — Woodard, Emhardt, Henry, Reeves and Wagner LLP

(57) ABSTRACT

Among other things, there are disclosed embodiments of belts or bands that can be used in treatments for tricuspid valve regurgitation. In some embodiments, such belts may be heat-set in a particular configuration to effectively decrease tricuspid annulus when deployed around the atrio-ventricular groove. Embodiments include one or more tensioning sutures for applying cinching or tightening to belts when deployed, and structure for effectively distributing force during such tightening.

20 Claims, 7 Drawing Sheets

(52) U.S. Cl.
CPC ............... *A61B 2017/0496* (2013.01); *A61F 2220/0075* (2013.01); *A61F 2230/0065* (2013.01); *A61F 2250/001* (2013.01)

(58) Field of Classification Search
CPC ....... A61F 2/2442–2451; A61B 5/6831; A61B 17/0487; A61B 2017/0496
See application file for complete search history.

(56) References Cited

U.S. PATENT DOCUMENTS

| | | |
|---|---|---|
| 2004/0064014 A1 | 4/2004 | Melvin et al. |
| 2004/0210240 A1* | 10/2004 | Saint ............... A61B 17/00234 606/139 |
| 2005/0059931 A1 | 3/2005 | Garrison et al. |
| 2010/0094425 A1* | 4/2010 | Bentley ............. A61B 17/0482 623/17.16 |
| 2011/0319917 A1 | 12/2011 | Ferrera et al. |
| 2012/0239085 A1* | 9/2012 | Schlotterback .... A61B 17/0401 606/228 |
| 2014/0330367 A1* | 11/2014 | Thapliyal ............. A61F 2/2415 623/2.11 |
| 2016/0038237 A1 | 2/2016 | Lederman et al. |
| 2016/0120647 A1 | 5/2016 | Rogers et al. |
| 2018/0049731 A1 | 2/2018 | Hardy et al. |
| 2018/0098850 A1 | 4/2018 | Rafiee et al. |

FOREIGN PATENT DOCUMENTS

| | | |
|---|---|---|
| WO | WO 2003/022131 A2 | 3/2003 |
| WO | WO 2004/052594 A2 | 6/2004 |
| WO | WO 2004/093730 A2 | 11/2004 |
| WO | WO 2019/089754 A1 | 5/2019 |

\* cited by examiner

BELT FOR APPLYING PRESSURE TO A BODILY ORGAN

The current disclosure general concerns devices for insertion into a patient's body to apply compression to an organ as a way of treating a condition of the patient. In particular, embodiments of a belt for application at least partially around an organ are disclosed. This invention was created in the performance of a Cooperative Research and Development Agreement with the National Institutes of Health, an Agency of the Department of Health and Human Services. The Government of the United States has certain rights in this invention.

BACKGROUND

In the treatment of tricuspid valve regurgitation (TR), it has been proposed to deliver a belt or band around the heart, and particularly into the atrioventricular (AV) groove of the heart. When positioned appropriately, the belt is cinched or otherwise tightened around the heart which narrows the tricuspid annulus and relieves the TR condition. To narrow the tricuspid annulus, the belt has to overcome the pressure from the heart, which may vary among patients, and which can be thought of as an unfortunate side-effect to be managed.

It has been proposed to use sutures to provide tension to the belt when necessary. Several problems have been noted with that approach. For example, when cinched the belt may generate too much pressure against the AV groove and/or coronary vessels or other tissues, which can constrain coronary flow and negatively affect heart function. Further, when a suture attached to a belt is used to cinch, it can be situated anywhere inside the belt, and move freely both axially and laterally. Control over the suture with respect to the belt, and with respect to biological structures of the heart, is thus lacking.

Overall, structures and methods for cinching a belt, and for ensuring that the belt minimizes any risk of coronary compression (e.g. compression of vessels to limit or prevent flow), are needed.

SUMMARY

Among other things, there are disclosed devices and methods for treating conditions including tricuspid valve regurgitation. Such devices include a band or belt for placement along the AV groove of the heart, which can include a heat-settable mesh tube having a first open end and a second open end and a lumen passing through the tube from the first open end to the second open end along a longitudinal axis of the tube. The tube may be configured longitudinally in a loop so as to be placed around the heart and along the AV groove. A first suture portion is within the tube, and is fixed to the tube adjacent the first open end and extends through the lumen toward the second open end. The first suture portion can be connected to the tube within the lumen by a plurality of holding elements so that the first suture portion is longitudinally movable through the holding elements with respect to the tube. In some embodiments, a second suture portion is within the tube and parallel to and spaced from the first suture portion. The second suture portion may be fixed to the tube adjacent the first open end and extend through the lumen toward the second open end. The second suture portion may be connected to the tube within the lumen by a plurality of holding elements so that the second suture portion is longitudinally movable through the holding elements with respect to the tube. Pulling the first and/or second suture portions cinches the tube to reduce an area of the loop so that the tube compresses longitudinally in at least selected locations along the tube.

In certain embodiments, the first suture portion and second suture portion each extend through the second open end of the tube to provide respective parts of the first and second suture portions that are outside the tube and able to be pulled to cinch the tube. Alternatively, the first suture portion and second suture portion can be parts of a single tensioning suture, having a middle portion between the first suture portion and second suture portion. A locking suture may be attached to the middle portion of the tensioning suture. A ring may be within the tube and adjacent the second open end, and in such cases the tensioning suture may fold over and through the ring, so that the first and second suture portions are on one side of the ring and the middle portion is on the other side of the ring. Embodiments of a ring may include a rounded engagement portion around which the tensioning suture is folded, and/or first and second linear sides that parallel the tube adjacent the second open end. The first and second linear sides may be connected to the tube by one or more respective holding elements. A locking suture can include a plurality of protrusions for use in holding tension applied to the locking suture and transmitted to the first and second suture portions. In one example, the locking suture has a length within the tube and a portion exiting the tube through the first open end, and the protrusions are on up to the full length of the locking suture within the tube and next to the first open end, and are not otherwise on the length of the locking suture within the tube.

Examples of the mesh of the tube are heat-settable materials, such as nitinol. Embodiments include the mesh being heat-set so that when the tube reaches body temperature, its cross section assumes a barbell shape, an ellipse or a flat ribbon shape. Further examples include the mesh being heat-set so that when the tube reaches body temperature, it assumes a shape with a first region having a first hoop diameter and first cross sectional dimension, and a second region having a second hoop diameter and second cross sectional dimension. The first hoop diameter may be greater than the second hoop diameter, and the first cross sectional dimension may be greater than the second cross sectional dimension. A medial portion between the first and second regions can include a contour adapted to conform to at least part of the atrioventricular groove. Another example can include the mesh being heat-set so that when the tube reaches body temperature, it assumes a saddle shape having one or more lower rounded contoured regions. At least one of the lower rounded contoured regions can be adapted to fit closely within the AV groove.

The disclosed structures minimize the risk of coronary compression as the compression belt is tensioned, and methods are disclosed to distribute applied forces of the belt over a sufficiently wide arc of the AV groove so as not to compress a coronary artery too much, while still achieving a therapeutic benefit in reducing regurgitation in the tricuspid and/or mitral valves. Embodiments of belts as disclosed herein should not exert an inward pressure (i.e. toward the heart) that is greater than coronary arterial pressure during ventricular diastole, when coronary flow is expected to be highest. Such embodiments should be shaped and/or configured to minimize any trauma to adjacent structures (e.g. no sharp edges on the belt), and to minimize risk of sliding on or around the heart once the belt is placed and cinched (if necessary). Some belt embodiments as disclosed may control the position of a suture or other tensioning element so as to optimally distribute force or pressure exerted by or otherwise associated with the tensioning element. In particular embodiments, the ends of the belt are configured to be easily pulled into a delivery catheter or other device (e.g. tapered), if retraction or correction is needed. Some belt embodiments are stretchable or compressible so as to compactly fit over a delivery frame and into a delivery catheter or other device, and will then take on a desired shape or configuration when deployed, which shape or configuration will effectively distribute tension, pressure or forces.

DETAILED DESCRIPTION OF THE ILLUSTRATED EMBODIMENTS

Figure 1:
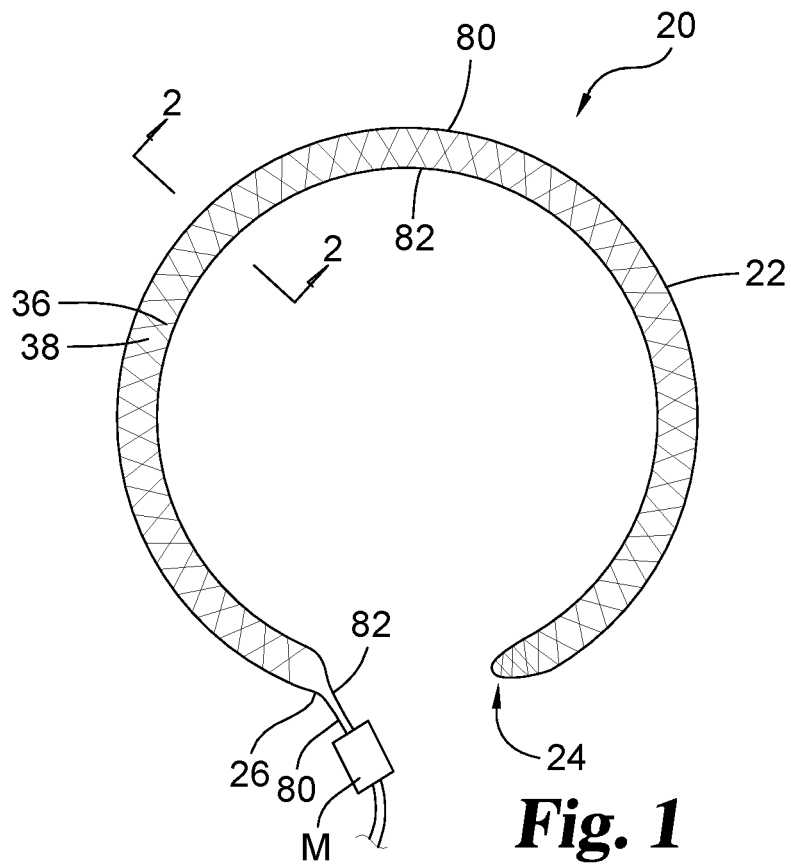
FIG. 1 is a top plan view of a belt according to embodiments disclosed herein.
Figure 2:
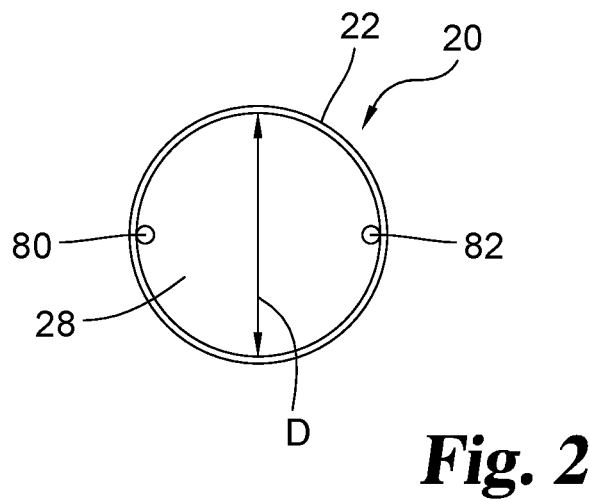
FIG. 2 is a cross-sectional view of the belt in FIG. 1, taken along the lines II-II and viewed in the direction of the arrows.
Figure 1A:
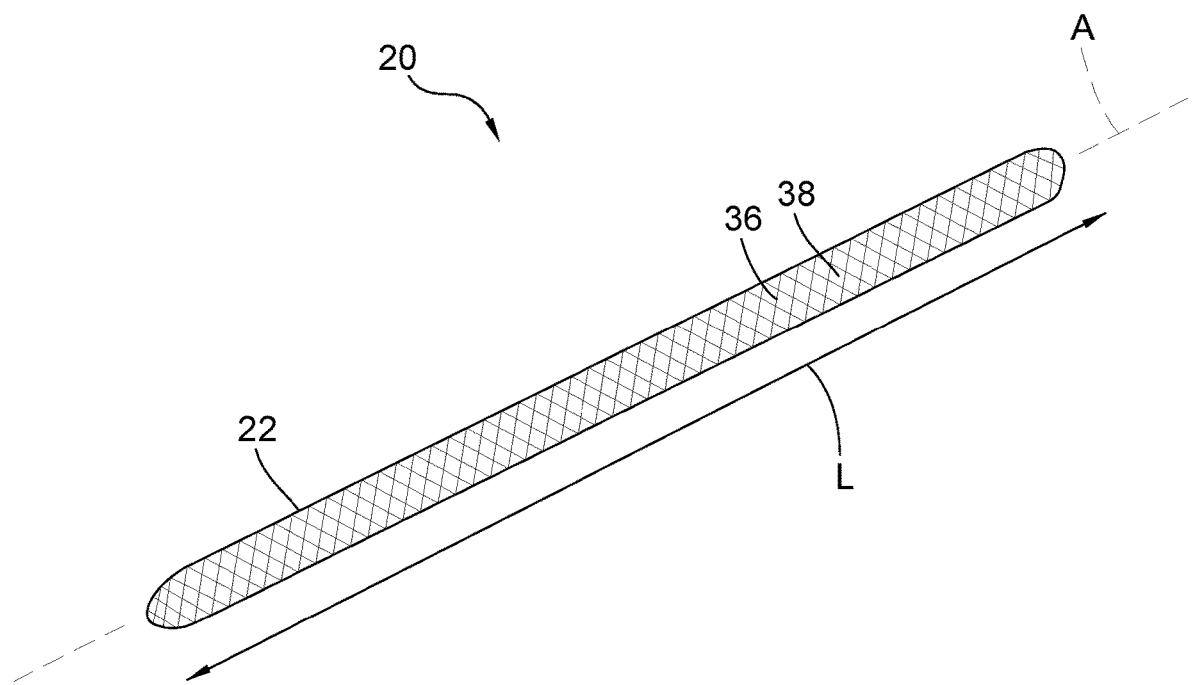
FIG. 1A is a perspective view of a mesh tube for a belt as in FIG. 1.

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the disclosure is thereby intended. Any alterations and further modifications in the described embodiments and any further applications of the principles of the present disclosure as described herein are contemplated as would normally occur to one skilled in the art to which the disclosure relates.

Referring now generally to the drawings, there is shown an embodiment of a belt 20 for use in applying compression to a bodily organ. As will be discussed below, belt 20 may be particularly prepared for application to the atrioventricular (AV) groove of the heart in treatment of tricuspid valve regurgitation (TR) conditions. While the disclosure herein may focus at times on that use and placement, it will be understood that the structures and methods disclosed may be used for a number of conditions, treatments, implants or purposes.

Belt 20 in the illustrated embodiment is a flexible mesh tube 22 of biocompatible material with opposed open ends 24, 26 and a natural diameter (i.e. a diameter that the tube has when not under stress or after being heat-set) around an internal volume or lumen 28 that extends between tapered or otherwise narrowed ends 24 and 26. One or more sutures are connected to belt 20 in order to provide tension to belt 20, as will be discussed further below. Such tension can cinch belt 20 in the AV groove for treatment of TR. The mesh of belt 20 may be formed of strands, wires or fibers 36 separated by interstices 38, or by cutting, etching, stamping or otherwise treating a thin sheet to remove portions, forming interstices 38. The mesh allows belt 20 to stretch lengthwise under tension along its length or central axis A to thereby decrease its diameter in the area stretched, and to be compressed lengthwise under compression or relaxation of tension along its length or central axis A to thereby increase its diameter in the area compressed.

It will be understood that the mesh of tube 22 may be made of a number of available natural or synthetic sturdy biocompatible materials. In a particular embodiment, the mesh of belt 20 is of nitinol, for example one or more individual nitinol wires (as strand(s) 36) fixed to and/or wound about each other to form interstices 38. Belt 20 in the embodiment illustrated in FIG. 1 has an original cylindrical shape with length L and diameter D measured across the longitudinal axis A. During manufacture, or at least prior to use, embodiments of belt 20 made of a heat-settable materials (e.g. nitinol) can be heat-set into a configuration that will be assumed when deployed in the body. In that example, belt 20 has its original (e.g. cylindrical) form at room temperature, is packed for delivery, and assumes the heat-set configuration when inserted into the body and its temperature is or approaches body temperature.

As a particular example of a desirable heat-set configuration, belt 20 is shown in FIG. 3 in a heat-set flat, ribbon shape. The flat ribbon shape may be heat-set into the nitinol mesh so that belt 20 has a desired width w (from side 40 to side 42) in its deployed state to go with the initial length L. It has been determined what the width w should be set as indicated below in order to keep the pressure from belt 20 from exceeding coronary arterial pressure during ventricular diastole, for example about 30 mmHg. The stress on a cross section of belt 20 for a particular tensile force F is $\sigma_0 = F/(tw)$, where t is the thickness of the mesh of belt 20 and w is the width of belt 20 defined above. The hoop stress equation relates that stress to a desired pressure P as $\sigma_0 = Pr/t$, where t is as defined above and r is the radius of the AV groove. Setting those representations of cross-sectional stress equal to each other gives $F/tw = Pr/t$. Cancelling and rearranging provides $w = F/Pr$. With an experimentally-determined tensile force of 0.4 pounds (1.8 N), a vascular pressure of 0.58 psi (30 mmHg), and a radius of the AV groove of 2 inches (51 mm), the width w of the belt 20 is determined to be 0.35 inches (8.9 mm). It will be understood that different values for the width w of belt 20 will be determined by the above method for variations with respect to a particular patient, such as differences in the AV groove radius or differences in vascular pressure. Accordingly, a belt 20 having a width w suited to the particular patient may be custom-made. That width w is configured by heat-setting belt 20, e.g. one of braided nitinol wires, so that when heat is applied by the body (i.e. body temperature), belt 20 acquires a configuration with width w.

Figure 3A:
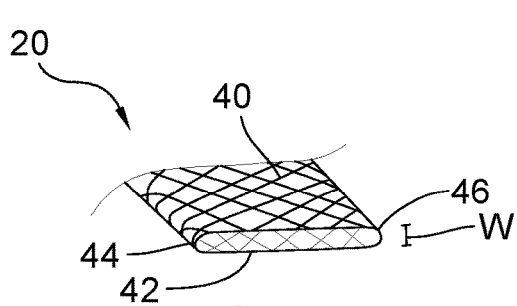
FIG. 3A is a perspective view of a cross-section of an embodiment of a belt of FIG. 1 in a particular set shape.
Figure 3B:
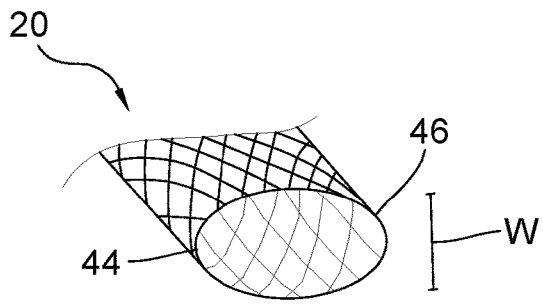
FIG. 3B is a perspective view of a cross-section of an embodiment of a belt of FIG. 1 in a particular set shape.

Preferably, belt 20 is heat-set to assume a flattened state, as in the prior example, so as to distribute the forces from the tensioning member to the belt. Flattening of the original cylindrical cross-section ranges from simply ovalizing the cross-section (FIG. 3A, a relatively high width w) to making a ribbon-like cross-section in which opposing sides 40, 42 of belt 20 are parallel to each other and closely adjacent to each other (FIG. 3B, a relatively low width w). In FIG. 3A, belt 20 is shown with an oval or elliptical cross section, with edges 44, 46 intersecting and separated by a major axis, and a middle portion between edges 44, 46, with width w being along or at least substantially parallel to a minor axis. In FIG. 3B, likewise edges 44, 46 intersect and are separated by a major axis, and width w is along or parallel to a minor axis. Edges 44, 46 provide locations for one or more sutures for tightening, as will be discussed further below.

Figure 4:
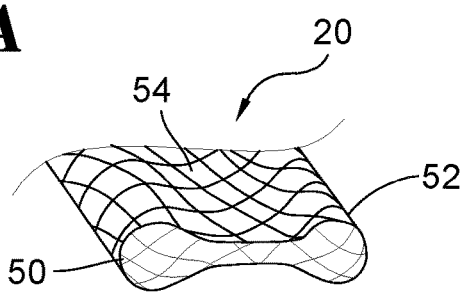
FIG. 4 is a perspective view of a cross-section of an embodiment of a belt of FIG. 1 in a particular set shape.

In particular embodiments, flattened belt 20 may be heat-set with enlarged, rounded edges 50, 52 on either side of the longitudinal axis A. In cross-section, this example of belt 20 looks like a dog bone or a barbell. As one example, the middle portion 54 of belt 20 between edges 50, 52 is flat, having the mesh at least approximately planar in each side 40, 42 between edges 50, 52, with those sides 40, 42 close to or touching each other side. Edges 50, 52 are round or curved, for example having a circular or oval cylindrical cross-section. In some illustrated embodiments (e.g. FIG. 4), edges 50, 52 have the same configuration as each other. Enlarged edges 50, 52 provide additional surface area to engage and grip the underlying tissue in the AV groove. Edges 50, 52, since they are rounded, reduce the potential for sharp corners or other surfaces that may cause any trauma to adjacent heart tissue. Since appendages or lobes of the atria may overhang belt 20 in the AV groove, a lack of such surfaces is preferred.

Figure 5:
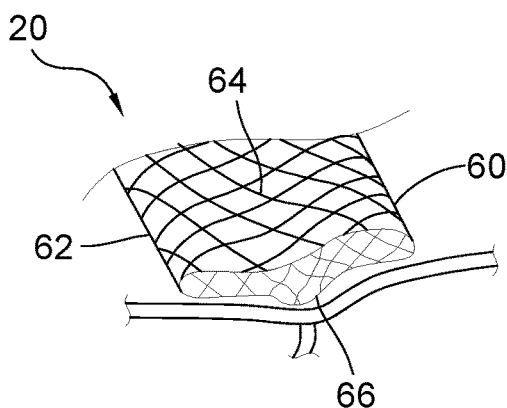
FIG. 5 is a perspective view of a cross-section of an embodiment of a belt of FIG. 1 in a particular set shape.

In another embodiment, belt 20 is heat set with a cross-section that creates a region 60 with a larger hoop diameter on one side, and a region 62 with a tighter/smaller hoop diameter. Region 60 is designed for placement over the ventricular walls, which are thicker than atrial tissues, and also have a higher chamber pressure. The thicker cross-section of region 60 has the advantage of more secure hold to the ventricular tissue, and the higher chamber pressure will withstand that thicker material. Region 62 is designed for placement over the thinner AV groove and atrial walls with their lower chamber pressure. The thinner region 62 can allow a medial portion 64 of belt 20 to more closely fit in the AV groove. Medial portion 64, as seen in the example of FIG. 5, can include a contour 66 in side 42 that conforms to at least part of the AV groove.

In another embodiment, belt 20 is heat-set with a ring shape with or approximating a natural curve of the exterior of the heart, so that belt 20 can have a natural location or fit around the heart. For example, an image of the heart may be taken so as to model the organ, and that imaging used to create a curve in belt 20, which is then heat-set into belt 20. Such an embodiment eases deployment, as belt 20 will assume the shape of the heart when deployed. A belt 20 in that shape will fit better over the heart, akin to fitting an oval peg into a hole with corresponding size and shape, and will conform better to the contours of the heart prior to a final tensioning of belt 20.

Figure 6:
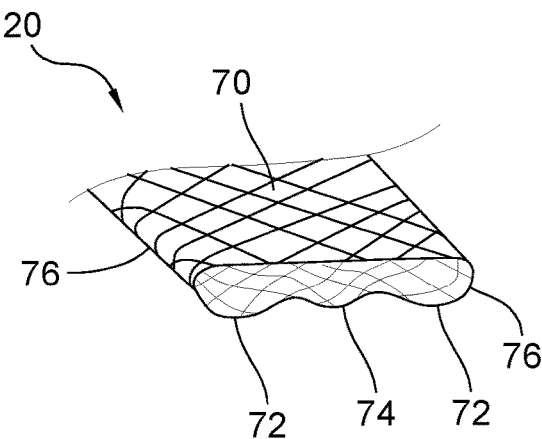
FIG. 6 is a perspective view of a cross-section of an embodiment of a belt of FIG. 1 in a particular set shape.

In another embodiment, belt 20 is heat-set with a three-lobed or saddle shape. FIG. 6 is an example cross sectional shape that would allow the passage of three sutures, e.g. one along each lobe, so as to distribute the load laterally along the AV groove. The shape addresses the fact that the AV groove itself does not lie in a single plane. A shape of belt 20 as in FIG. 6 allows it to more naturally sit in the AV groove upon deployment. Further, when used with three tensioning sutures, the lobes keep the sutures separated and distribute the compressive forces applied by the sutures. In that example, belt 20 has an upper flat region 70 and one or more lower contoured regions, e.g. two side lobes 72 and a middle lobe 74. Middle lobe 74 is rounded, e.g. part-cylindrical or a rounded ridge, that is adapted to fit within, and preferably closely within, the AV groove. Side lobes 72 are rounded, e.g. with at least part having essentially the same curvature as middle lobe 74, and edges 76 are also rounded. Such edge regions, as noted above with respect to (dog-bone version), provide more secure engagement without sharp corners. More generally, the pathway of belt 20 can be heat set to a non-planar three-dimensional shape that better traces the pathway of the AV groove in the heart.

In any of these embodiments, belt 20 may be heat-set to provide a greater width w of belt 20 for regions of the belt that are to be placed over areas of the heart where arteries are (more likely) to pass underneath. That greater width allows for a relatively smaller pressure in that area of belt 20 when tensioned, and such an area should be over regions of the heart where arteries pass. Belt 20 may be narrower in width in portions that will lie over or near the tricuspid annulus of the heart. That narrower width may provide a relatively greater pressure in that area of belt 20 when tensioned, and thus directs that greater pressure where needed to treat tricuspid regurgitation.

In any of the embodiments of belts disclosed herein, tension is applied by one or more sutures through the belt. By "sutures" is meant not only the common definition, but any biocompatible line or filament having flexibility and tensile strength sufficient to be passed through a belt for use in procedures such as TR treatment and pull it in tension when deployed, as discussed herein. Further, "sutures" means not only wholly separate items but also portions of one or more such items. Pulling or otherwise placing the suture(s) in tension applies compression to the belt, thereby applying compression to the AV groove of the heart.

Figure 7:
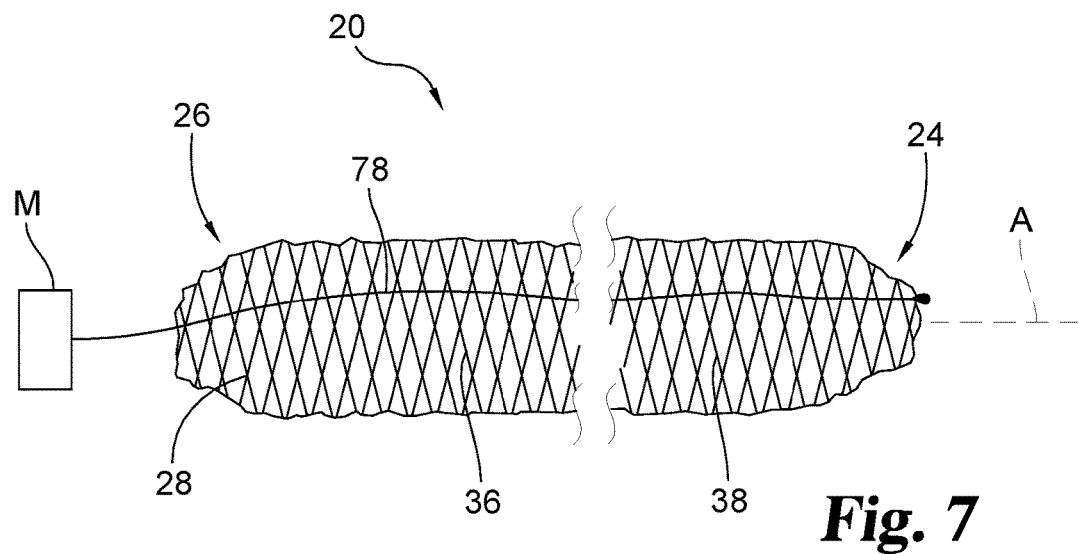
FIG. 7 is a plan view of an embodiment of a belt with a single tensioning suture.

In embodiments in which only one tensioning suture is attached or otherwise connected to belt 20 (e.g. FIG. 7), the suture 78 may float within belt 20 through lumen 28. One end of the tensioning suture 78 is fixed to belt 20 at or near one end 24 of belt 20 (and a locking mechanism M attached or otherwise connected to belt 20) in particular embodiments. The suture 78 passes through lumen 28 and out of end 26 of belt 20 and through the locking mechanism M. The tensioning suture 78 within belt 20 can move both axially and laterally with respect to belt 20. Pulling on the end of the tensioning suture 78 that passes through the locking mechanism, with the other end fixed to belt 20, moves part of the suture 78 through belt 20. End 24 is pulled along axis A along with suture 78, to reduce the length of belt 20 and placing it in tension. Activation of the locking mechanism M holds the suture 78, and belt 20, with that tension around the heart.

Figure 8:
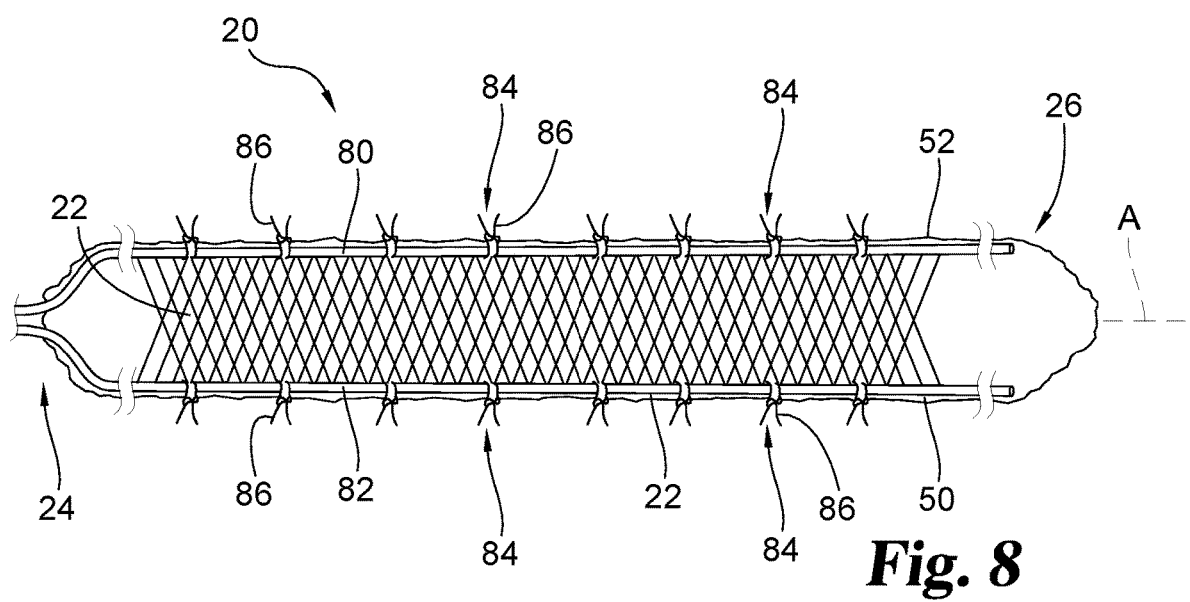
FIGS. 8-10 are plan views of embodiments of a belt with two tensioning suture portions.

In the embodiment illustrated in FIG. 8, belt 20 includes two parallel sutures or suture portions 80, 82 within it to provide tension. It has been found that the use of two sutures 80, 82 is more effective in providing steady tension to belt 20, and in distributing the pressure or force when cinching or tightening belt 20 around the heart, than can be done with a single suture floating within belt 20. For example, application of force through two separated sutures reduces or eliminates risk of turning or pivoting of belt 20 during tightening or cinching, e.g. by turning belt around an edge (e.g. 44, 46, 50 or 52) so that flat belt 20 rises or stands on one edge. It has also been found that use of two sutures 80, 82 with belt 20 is more effective when sutures 80, 82 are confined laterally, i.e. maintained apart from each other. It has been found that two floating sutures tend to stay together, due to minimized potential energy, or being pulled together during deployment or cinching of belt 20. When the sutures stay together, they tend to behave like a single, thicker suture, which loses the force application and distribution and other benefits of having two sutures.

Sutures 80, 82 are attached to belt 20 in locations opposed to each other across the longitudinal axis of belt 20, and in the illustrated embodiment, sutures 80, 82 are attached to the inside of belt 20. In embodiments in which belt 20 is heat-set to a particular shape, sutures 80, 82 are placed after heat-setting. A series of holding elements 84 surround sutures 80, 82 in various locations along belt 20. In a particular embodiment, elements 84 are threads or filaments that tie around the respective suture 80, 82 and through the mesh of belt 20. For example, a holding element 84 in the form of a filament 86 is threaded through the mesh, around suture 80, and back through mesh, one or more times, and then is knotted, heat-fused, or otherwise secured. In the illustrated embodiment, filament 86 is threaded or looped around suture 80 at least twice, and secured at or adjacent belt 20, e.g. on an outer surface of belt 20. It will be understood that securing (e.g. by knotting) filament 86 with respect to itself and to belt 20 retains some slack or flexibility in filament 86 to form an opening or passage 88 through each holding element 84 that allow suture 80 to move longitudinally through the passages 88 of respective holding elements 84 with minimal resistance. Similar or identical holding or securing elements 84 are present for suture 82.

Figure 9:
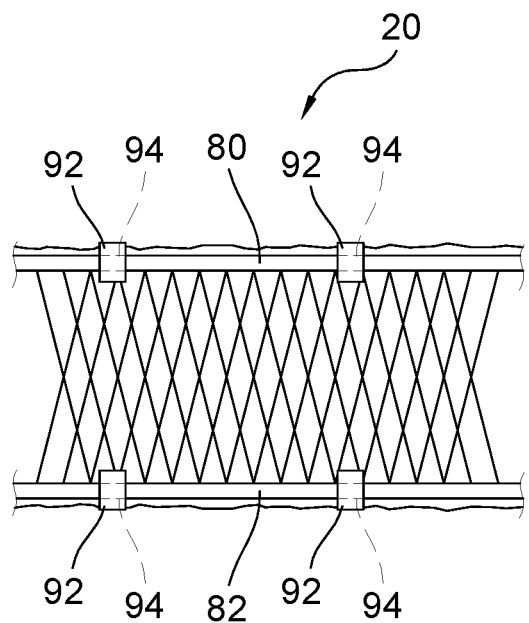
Figure 10:
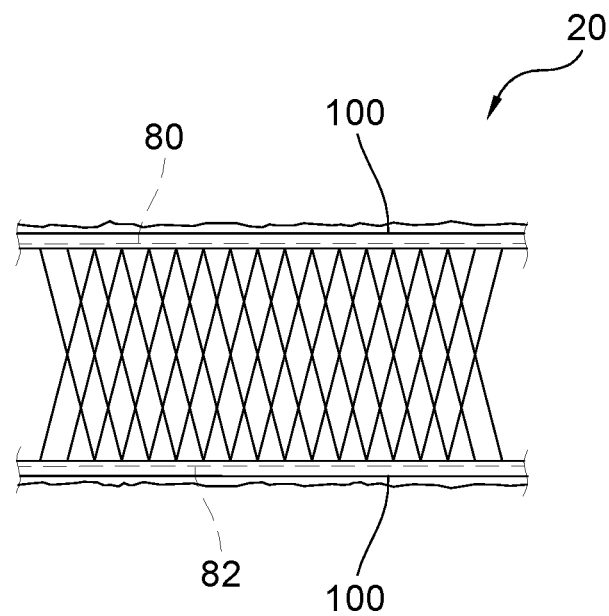

In other embodiments, holding elements may be or include rings, tubing or sheath attached to belt 20. Filaments as discussed above behave as rings. In an example of belt 20 made of nitinol wires in a mesh, internal guide rings (92 in FIG. 9) may be formed using the individual wire(s) that form the mesh of belt 20 (e.g. such rings may be created when the mesh for belt 20 is formed). Rings 92 have an opening or passage 94 sized to allow suture 80 or 82 to pass through rings longitudinally with minimal resistance. The metallic surface of rings 92 may provide significantly less resistance to longitudinal passage of sutures 80, 82 than filament holding elements 84, particularly if the metal (e.g. nitinol wires) are smoothed, as is indicated for use in belt 20 so as to limit or eliminate damage or irritation to adjacent tissue. In other embodiments, a tube or sheath 100 may be attached to the inside of belt 20 (e.g. FIG. 10), in similar locations to individual filament holding elements 84 or ring holding elements 92, which have a passage sized to allow suture 80 or 82 to pass through rings longitudinally with minimal resistance. Several individual tubes may be placed within belt 20 and separated by gaps from each other, particularly if such tubes are less longitudinally compressible than belt 20, or if a single tube 100 is used as a holding element, such a tube should be compressible so as not to limit the cinching of belt 20 when placing it in tension.

Securing or holding elements 84 are evenly spaced, in the illustrated embodiment, along belt 20. Because sutures 80, 82 are intended to remain in tension or essentially linear in holding elements 84 along belt 20, holding elements 84 may be spaced relatively far from each other, e.g. up to 5 millimeters, up to 10 millimeters, up to 15 millimeters, up to 20 millimeters from each other in particular embodiments, or close enough to each other so that any slack that may exist in one or both of suture 80, 82 does not allow one of sutures 80, 82 to touch the other when belt is being deployed. Further, the locations of holding elements 84 are shown in one embodiment as staggered along sutures 80, 82, i.e. a plane perpendicular to the longitudinal axis of belt 20 through one holding element 84 holding one suture 80 will pass between holding elements 84 holding the other suture 82, and in a particular embodiment will be halfway between holding elements 84 holding the other suture 82 (e.g. FIG. 8). That staggered condition allows belt 20 to be folded, compressed or otherwise packed into a delivery device with holding elements 84 offset from each other, providing a lower profile for the delivery device. In other embodiments, holding elements 84 may be symmetric or only very slightly offset (e.g. by 1-3 millimeters, so that the above noted plane through a holding element with suture 80 may pass immediately next to a holding element with suture 82) in belt 20. In such a case, tension by sutures 80, 82 is applied to belt 20, via holding elements 84, at or near the same locations on sides 40, 42 of belt 20.

In other embodiments, one or both of sutures 80, 82 may be woven through the mesh of belt 20 along two lines each lateral of the longitudinal axis of belt 20. In one example, suture 80 may be fixed at one end 24 of the interior of belt 20, passed out through the mesh of belt 20 and run along the outside of belt 20 for a length, then passed back through the mesh to the inside of belt 20 for a length (which may be the same or a different length as was run along the outside of belt 20). That weaving continues through the length of belt 20. Suture 82 may be similarly or identically woven through the other side of belt 20. It has been found that such weaving produces relatively high friction forces between suture(s) 80, 82 and belt 20, and when suture(s) 80, 82 are cinched, the tension provided to belt 20 may not be homogeneous, so that part of belt 20 contracts around the heart, while other parts may remain relatively loose. Thus, weaving suture(s) 80, 82 through belt 20 may be effective under certain circumstances, but other embodiments disclosed herein operate in a more effective fashion.

Figure 11:
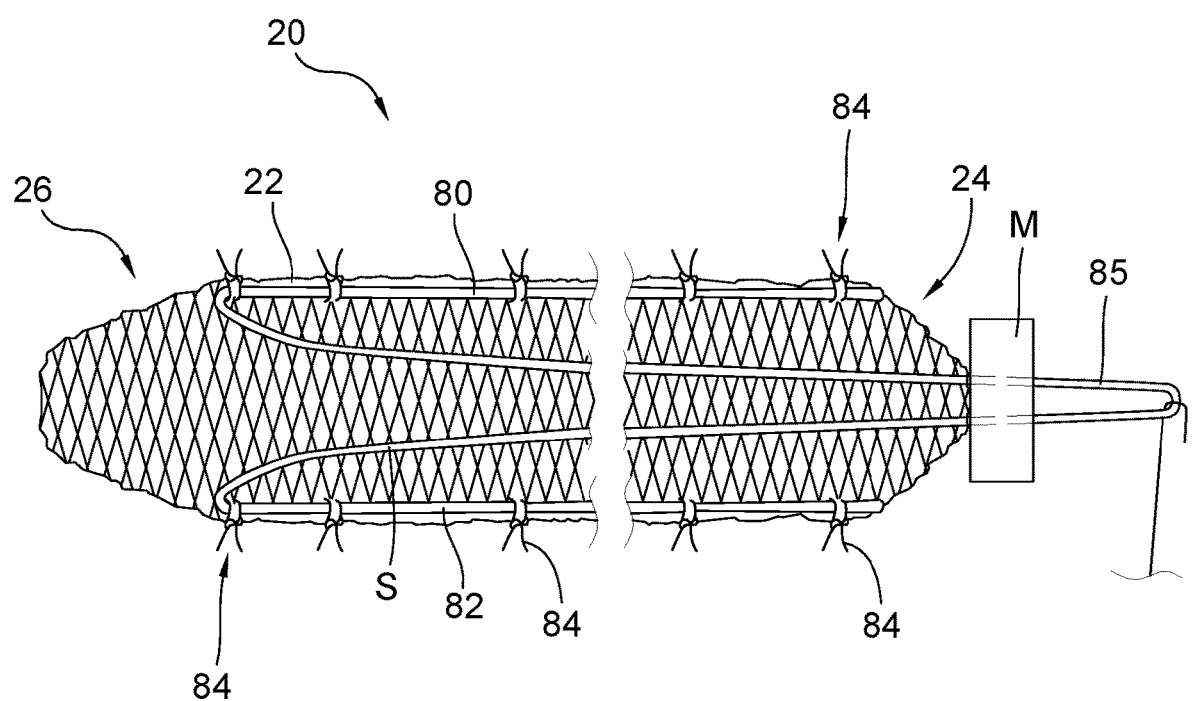
FIG. 11 is a plan view of an embodiment of a belt with two tensioning suture portions with a middle loop.

In another embodiment, shown in FIG. 11, a belt 20 is shown that is similar or identical to embodiments of belt 20 described above, including mesh tube 22 with narrowed ends 24, 26. In this embodiment, a single suture S extends through belt 20, with a first suture portion 80 extending along one side or edge of belt 20 and a second suture portion 82 extending along an opposite side or edge of belt 20. As with other belt embodiments described herein, suture S is fixed to tube 22 at end 24, e.g. an end of suture portion 80 and an end of suture portion 82 are respectively fixed to tube 22, as indicated in FIG. 11, or to a locking mechanism M adjacent or connected to tube 22. From those fixed ends, each suture portion 80, 84 runs toward end 26, and are held to tube 22 by one or more holding elements 84, as discussed above. When suture portions 80, 82 are near or reach end 26 in this embodiment, suture S loops back through lumen 28 of belt 20 to form loop 85. Loop 85 in this embodiment extends through lumen 28 and out through end 24 (and through locking mechanism M, if present) to an exterior of tube 22 of belt 20. Loop 85 can be connected to a tensioning line T, as by a hook, grip or other structure, that may be part of a system for delivering belt 20. Following deployment of belt 20, as generally described below, tensioning line T can preferably be disengaged from loop 85 and withdrawn. This embodiment provides redundancy, so that if one of suture portions 80, 82 fails, the other suture portion remains to provide tension to belt 20.

In another embodiment, belt 20 (FIG. 12) is configured the same as embodiment(s) above, with holding elements 184 that are similar or identical to holding elements 84 described above. It will be understood that belt 20 may be made, shaped and/or configured as described above with respect to particularly-shaped or set embodiments. A first suture or suture portion 180 passes through holding elements 184 along one side 140 of belt 20, and a second suture or suture portion 182 passes through holding elements 184 along another side 142 of belt 20, e.g. a side opposite from suture or suture portion 180 across the longitudinal axis A of belt 20. A locking suture 210 is connected to suture portions 180, 182 at or adjacent one end 226 of belt 20, and the suture portions 180, 182 pass through a ring 212 at or adjacent that end 226 of belt 180.

Figure 12:
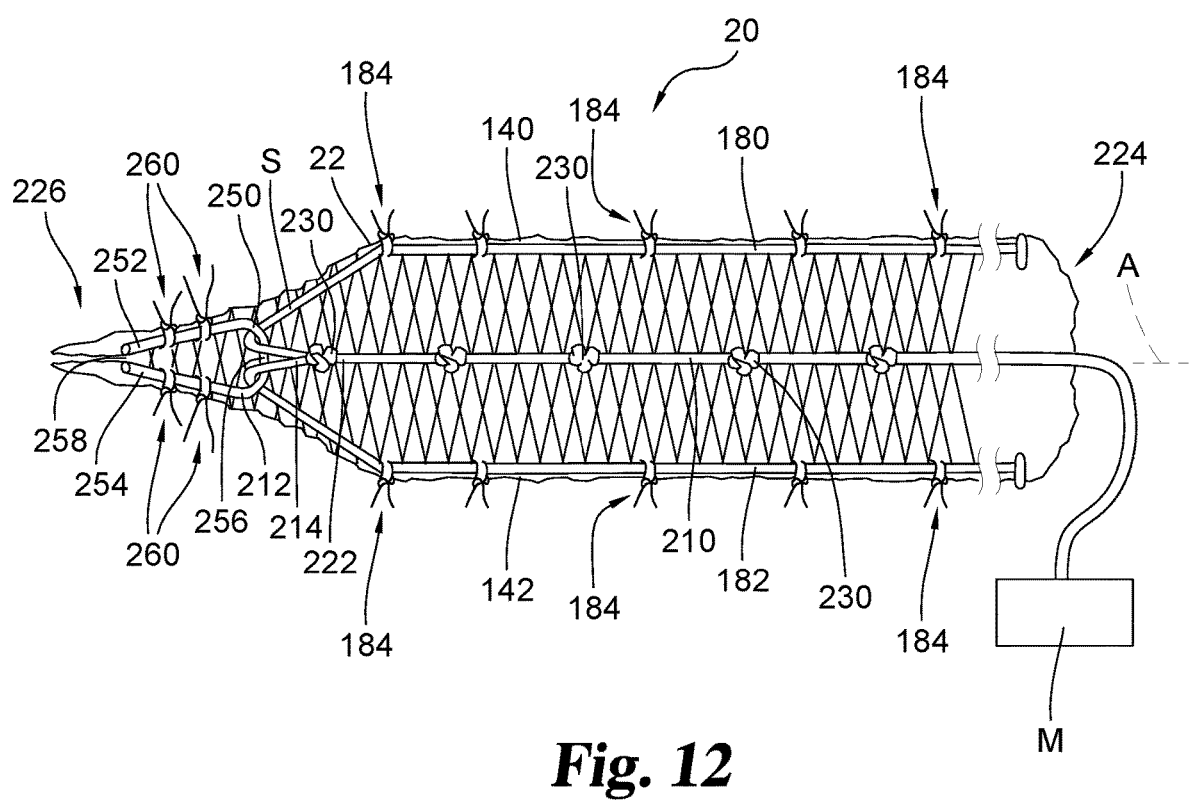
FIG. 12 is a plan view of an embodiment of a belt with two tensioning suture portions with a middle loop and additional structure.

In the illustrated embodiment, suture portions 180, 182 are part of a single tensioning suture S. Suture portions 180, 182 are each fixed to end 224 of belt 20 (e.g. by a blanket stitch), as described above with respect to suture 80, 82. Suture portion 180 passes through holding elements 184 on one side of belt 20 (e.g. the top as seen in FIG. 12), then a central loop 214 of the suture S passes through ring 212 at or near the other end 226 of belt 20, and the rest of the suture S passes through holding elements 184 on the other side of belt 80 (e.g. the bottom as seen in FIG. 12) and is fixed at end 224 of belt 20. Loop 214 that passes through ring 212 is fixed to an end 222 of locking suture 210, so that the tensioning suture S folds over a portion of ring 212 (i.e. bending 180 degrees around and through ring 212), with portions 80, 82 on one side of ring 212 and loop 214 on the other. It will be understood that in other embodiments suture portions 80, 82 may be separate tensioning sutures, each of which pass through ring 212 as described above and attach to locking suture 210.

Locking suture 210 in the illustrated embodiment includes a series of knots, beads or other protrusions 230, which in the illustrated embodiment are evenly spaced along the whole length of suture 210 within belt 220 and into a locking mechanism M (as described above). In other embodiments, protrusions 230 may be present only in part of suture 210, e.g. of the part of locking suture 210 within belt 220 and into locking mechanism M, at least the one-third to one-half that is furthest from ring 212. It has been found that the tensioned or cinched belt (e.g. belt 20) may need to have a length between 60 and 80 percent of the initial length L of the belt, and so a length of suture 210 (e.g. between 80 and 40 percent of the initial length of suture 210 within the belt) will have to pass out of the belt and to or through a locking mechanism M. Accordingly, placing protrusions on at least the 40 to 80 percent of suture 210 that is adjacent mechanism M and entering belt 20, and therefore has the potential to be pulled through the end of the belt and a locking mechanism, is advantageous.

Ring 212 in the illustrated embodiment has a rounded (e.g. circular) portion 250 over which tensioning sutures or suture portions 180, 182 are folded, and two linear sides 252, 254 that join to each other and to rounded portion 250. Ring 212 may be made of a biocompatible wire or other sturdy material, and is relatively inflexible so as to be able to effectively transfer tension from locking suture 210 to tensioning suture portions 180, 182. The exterior surface 256 of ring 212 is rounded (e.g. made of wire that is circular in cross section) and smooth in certain embodiments, so as to reduce friction between ring 212 and tensioning suture portions 180, 182 during use. It has been found in experimental testing that the cross-sectional diameter of wire used in embodiments of ring 212 has a substantial effect on friction between ring 212 and suture portions 180, 182, and that for a suture of 0.35 millimeter diameter and made of ultra-high molecular weight polyethylene (UHMWPE), wire used to make ring 212 should have a diameter of 0.021 inches or larger.

Sides 252 and 254 are unitary or monolithic with rounded portion 250, and are linear in this embodiment, joining with each other at an apex 258. The linear nature of sides 252, 254 is intended to fit closely with the narrowing sides 240, 242 of belt 20 at end 226 of belt 20, and in a particular embodiment the angle between sides 252, 254 at apex 258 is between 5 and 30 degrees. Sides 252, 254 may be initially separate and be joined at apex 258, as by welding, adhesives or other techniques, or they may be formed joined with each other and with rounded portion 250. Ring 212 is held to the narrowing sides 240, 242 of belt 20 by holding elements 260, which may be similar or identical to embodiments of holding elements 84 described above.

The embodiment of belt 20, with ring 212, provides several advantages, including low friction between the tensioning suture 180, 182 and belt 20, and a locking suture 210 having protrusions 230 that has a low risk of becoming stuck to belt 20. The design will permit cinching of belt 20 up to about 50 percent of the original length of belt 20, which will provide sufficient decrease of tricuspid annulus in TR treatment. Also, as noted above with respect to FIG. 11, a failure in one suture 180 or 182, leaves the other to provide tension to belt 20.

Use of belt 20 will now be discussed in the context of placement in or along a patient's AV groove and tightening, for treatment of TR or other conditions. It will be understood that use of the disclosed structure in other locations or contexts is possible. Reference in the following discussion is particularly to the embodiment in FIG. 12. However, it will be understood that the methods described below are generally applicable to other embodiments of belt 20 described herein, the principal difference being the lack of ring 212 and/or a locking suture 210.

Belt 20 is delivered to the AV groove, as by a delivery system (not shown) that can include an introducer as disclosed in PCT/US2017/058245, filed Oct. 25, 2017, which is incorporated by reference herein in its entirety. Belt 20 exits the delivery system and is looped around the heart, and situated in the AV groove. Belt 20 and suture portions 180, 182 thus circle around the heart.

When placement of belt 20 is determined to be satisfactory, the user proceeds to tighten belt 20 to decrease tricuspid annulus on the heart around the AV groove. The user pulls on locking suture 210 using an appropriate tool (not shown), so that locking suture begins to exit end 224 of belt 20 and move through locking mechanism M. As locking suture 210 is pulled, loop 214 is also pulled, and tension in locking suture 210 is passed around ring 212 to tensioning suture portions 180, 182. Suture portions 180, 182 are thus pulled through their respective holding elements 184. Pulling suture portions 180, 182 reduces the radius of suture portions 180, 182 around the heart, forcing belt 20 inward against the heart, and the respective ends of suture portions 180, 182 that are fixed to end 224 of belt 20 compress the length of belt 20. As the length of belt 20 is compressed, the mesh of belt 20 transmits that compression into some expansion in width, providing flexibility so as to limit or reduce pressure exerted on coronary arteries or other structures.

Locking suture 210 is pulled until the desired amount of tricuspid annulus decrease is achieved. In particular embodiments, as noted above, that amount is achieved with a reduction in length of belt 20 to up to 60 percent of the original length of belt 20. Once the cinching or tightening is complete, locking mechanism M is activated to hold locking suture 210 in the tensioned condition. Removal of delivery and other tools and completion of the procedure can then be performed.

While the disclosure has been illustrated and described in detail in the drawings and foregoing description, the same is to be considered as illustrative and not restrictive in character, it being understood that only selected embodiments have been shown and described and that all equivalents, changes, and modifications that come within the spirit of the disclosures as defined herein or by the following claims are desired to be protected. It will be understood that features described particularly with respect to one or more specific structures or embodiments may be incorporated into or otherwise used with other structures or embodiments as disclosed herein.

The following numbered clauses set out specific embodiments that may be useful in understanding the present invention:

1. A belt for placement along the atrioventricular groove of the heart, comprising:
a mesh tube having a first open end and a second open end and a lumen passing through the tube from the first open end to the second open end along a longitudinal axis of the tube, the tube configured longitudinally in a loop so as to be placed around the heart and along the atrioventricular groove;
a first suture portion within the tube, the first suture portion fixed to the tube adjacent the first open end and extending through the lumen toward the second open end, the first suture portion connected to the tube within the lumen by a plurality of holding elements so that the first suture portion is longitudinally movable through the holding elements with respect to the tube;
a second suture portion within the tube and parallel to and spaced from the first suture portion, the second suture portion fixed to the tube adjacent the first open end and extending through the lumen toward the second open end, the second suture portion connected to the tube within the lumen by a plurality of holding elements so that the second suture portion is longitudinally movable through the holding elements with respect to the tube;
wherein pulling the first and second suture portions cinches the tube to reduce an area of the loop so that the tube compress longitudinally in at least selected locations along the tube.

2. The belt of clause 1, wherein the first suture portion and second suture portion each extend through the second open end of the tube to provide respective parts of the first and second suture portions that are outside the tube and able to be pulled to cinch the tube.

3. The belt of any of clauses 1-2, wherein the first suture portion and second suture portion are parts of a single tensioning suture, having a middle portion between the first suture portion and second suture portion, and further comprising a locking suture attached to the middle portion of the tensioning suture.

4. The belt of any of clauses 1-3, further comprising a ring within the tube and adjacent the second open end, wherein the tensioning suture folds over and through the ring, wherein the first and second suture portions are on one side of the ring and the middle portion is on the other side of the ring.

5. The belt of clause 4, wherein the ring includes a rounded engagement portion around which the tensioning suture is folded.

6. The belt of clause 4, wherein the ring includes first and second linear sides that parallel the tube adjacent the second open end, the first linear side connected to the tube by at least one holding element, and the second linear side connected to the tube by at least one holding element.

7. The belt of any of clauses 3-6, wherein the locking suture includes a plurality of protrusions for use in holding tension applied to the locking suture and transmitted to the first and second suture portions.

8. The belt of clause 7, wherein the locking suture has a length within the tube and a portion exiting the tube through the first open end, and wherein the protrusions are on up to the full length of the locking suture within the tube and next to the first open end, and are not otherwise on the length of the locking suture within the tube.

9. The belt of any of clauses 1-8, wherein the mesh is nitinol.

10. The belt of any of clauses 1-9, wherein the mesh is heat-set so that when the tube reaches body temperature, its cross section assumes a barbell shape.

11. The belt of any of clauses 1-9, wherein the mesh is heat-set so that when the tube reaches body temperature, its cross section assumes an elliptical or oval shape.

12. The belt of any of clauses 1-9, wherein the mesh is heat-set so that when the tube reaches body temperature, it assumes a flat ribbon shape.

13. The belt of any of clauses 1-9, wherein the mesh is heat-set so that when the tube reaches body temperature, it assumes a shape with a first region having a first hoop diameter and first cross sectional dimension, and a second region having a second hoop diameter and second cross sectional dimension, and wherein the first hoop diameter is greater than the second hoop diameter, and the first cross sectional dimension is greater than the second cross sectional dimension.

14. The belt of clause 13, wherein a medial portion between the first and second regions includes a contour adapted to conform to at least part of the atrioventricular groove.

15. The belt of any of clauses 1-9, wherein the mesh is heat-set so that when the tube reaches body temperature, it assumes a saddle shape having one or more lower rounded contoured regions, and wherein at least one of the lower rounded contoured regions is adapted to fit closely within the atrioventricular groove.

16. The belt of any of clauses 1-15, wherein the two suture portions are each part of a respective separate suture.

17. The belt of any of clauses 1-16, wherein the two suture portions are connected to form a loop.

18. The belt of clause 17, wherein the loop is connected to an elongated element at least partially exterior to the belt, the elongated element being one of a locking suture and a delivery filament.

Structures or other features specified in the above clauses may be included singly or in any combination in the inventive devices, along with other structures or features described above with respect to any embodiment.

What is claimed is:

1. A belt for placement along the atrioventricular groove of the heart, comprising:
a mesh tube having a first open end, a second open end and a lumen passing through the tube from the first open end to the second open end along a longitudinal axis of the tube, the tube configured longitudinally in a loop so as to be placed around the heart and along the atrioventricular groove;
a first suture portion within the tube, the first suture portion fixed to the tube at a first location adjacent the first open end and extending through the lumen toward the second open end, the first suture portion connected to the tube within the lumen by a first plurality of holding elements so that the first suture portion is longitudinally movable through the first plurality of holding elements with respect to the tube;
a second suture portion within the tube and spaced from the first suture portion, the second suture portion fixed to the tube at a second location adjacent the first open end and extending through the lumen toward the second open end, the second location spaced from the first location, the second suture portion connected to the tube within the lumen by a second plurality of holding elements so that the second suture portion is longitudinally movable through the second plurality of holding elements with respect to the tube;

wherein pulling the first and second suture portions moves the first and second suture portions through the first plurality of holding elements and the second plurality of holding elements, respectively, and cinches the tube to reduce an area of the loop so that the tube compress longitudinally in at least selected locations along the tube.

2. The belt of claim 1, wherein the first suture portion and second suture portion each extend through the second open end of the tube to provide respective parts of the first and second suture portions that are outside the tube and able to be pulled to cinch the tube.

3. The belt of claim 1, wherein the mesh is nitinol.

4. The belt of claim 1, wherein the mesh is heat-set so that when the tube reaches body temperature, a cross section of the tube assumes a barbell shape.

5. The belt of claim 1, wherein the mesh is heat-set so that when the tube reaches body temperature, a cross section of the tube assumes an elliptical or oval shape.

6. The belt of claim 1, wherein the mesh is heat-set so that when the tube reaches body temperature, the tube assumes a flat ribbon shape.

7. The belt of claim 1, wherein the mesh is heat-set so that when the tube reaches body temperature, the tube assumes a shape with a first region having a first hoop diameter and first cross sectional dimension, and a second region having a second hoop diameter and second cross sectional dimension, and wherein the first hoop diameter is greater than the second hoop diameter, and the first cross sectional dimension is greater than the second cross sectional dimension.

8. The belt of claim 7, wherein a medial portion between the first and second regions includes a contour adapted to conform to at least part of the atrioventricular groove.

9. The belt of claim 1, wherein the mesh is heat-set so that when the tube reaches body temperature, the tube assumes a saddle shape having one or more lower rounded contoured regions, and wherein at least one of the lower rounded contoured regions is adapted to fit closely within the atrioventricular groove.

10. The belt of claim 1, wherein the first and second suture portions are each part of a respective separate suture.

11. The belt of claim 1, wherein the first and second suture portions are connected to form a loop.

12. The belt of claim 11, wherein the loop is connected to an elongated element at least partially exterior to the belt, the elongated element being one of a locking suture and a delivery filament.

13. The belt of claim 1, wherein the second suture portion within the tube is parallel to the first suture portion.

14. The belt of claim 1, wherein the mesh tube is comprised of braided nitinol wires, wherein the mesh tube is configured to stretch lengthwise under tension to thereby decrease a diameter of the mesh tube in an area of the mesh tube that is stretched, and wherein the mesh tube is configured to be compressed lengthwise under compression or relaxation of tension to thereby increase a diameter of the mesh tube in an area of the meshed tube that is compressed.

15. A belt for placement along the atrioventricular groove of the heart, comprising:
a mesh tube having a first open end, a second open end and a lumen passing through the tube from the first open end to the second open end along a longitudinal axis of the tube, the tube configured longitudinally in a loop so as to be placed around the heart and along the atrioventricular groove;
a first suture portion within the tube, the first suture portion fixed to the tube adjacent the first open end and extending through the lumen toward the second open end, the first suture portion connected to the tube within the lumen by a first plurality of holding elements so that the first suture portion is longitudinally movable through the first plurality of holding elements with respect to the tube;
a second suture portion within the tube, the second suture portion being parallel to and spaced from the first suture portion, the second suture portion fixed to the tube adjacent the first open end and extending through the lumen toward the second open end, the second suture portion connected to the tube within the lumen by a second plurality of holding elements so that the second suture portion is longitudinally movable through the second plurality of holding elements with respect to the tube;
wherein pulling the first and second suture portions cinches the tube to reduce an area of the loop so that the tube compress longitudinally in at least selected locations along the tube; and wherein the first suture portion and second suture portion are parts of a single tensioning suture having a middle portion between the first suture portion and second suture portion, and further comprising a locking suture attached to the middle portion of the tensioning suture.

16. The belt of claim 15, further comprising a ring within the tube and adjacent the second open end, wherein the tensioning suture folds over and through the ring, wherein the first and second suture portions are on one side of the ring and the middle portion is on the other side of the ring.

17. The belt of claim 16, wherein the ring includes a rounded engagement portion around which the tensioning suture is folded.

18. The belt of claim 16, wherein the ring includes first and second linear sides that parallel the tube adjacent the second open end, the first linear side connected to the tube by at least one holding element, and the second linear side connected to the tube by at least one holding element.

19. The belt of claim 15, wherein the locking suture includes a plurality of protrusions for use in holding tension applied to the locking suture and transmitted to the first and second suture portions.

20. The belt of claim 19, wherein the locking suture has a length within the tube and a portion exiting the tube through the first open end, and wherein the protrusions are on up to the full length of the locking suture within the tube and next to the first open end, and are not otherwise on the length of the locking suture within the tube.

* * * * *